(12) United States Patent
Evans et al.

(10) Patent No.: US 12,144,563 B1
(45) Date of Patent: Nov. 19, 2024

(54) ULTRASOUND-GUIDED PROCEDURES

(71) Applicant: Agitated Solutions Inc., Oakdale, MN (US)

(72) Inventors: Morgan Evans, Apple Valley, MN (US); Trent Christensen, Minneapolis, MN (US)

(73) Assignee: Agitated Solutions Inc., St. Paul, MN (US)

( * ) Notice: Subject to any disclaimer, the term of this patent is extended or adjusted under 35 U.S.C. 154(b) by 0 days.

(21) Appl. No.: 17/694,648

(22) Filed: Mar. 14, 2022

Related U.S. Application Data

(60) Provisional application No. 63/161,374, filed on Mar. 15, 2021.

(51) Int. Cl.
    *A61B 34/20* (2016.01)
    *A61B 8/08* (2006.01)

(52) U.S. Cl.
    CPC ............ *A61B 34/20* (2016.02); *A61B 8/0841* (2013.01); *A61B 8/481* (2013.01); *A61B 2034/2063* (2016.02)

(58) Field of Classification Search
    CPC ....... A61B 34/20; A61B 8/0841; A61B 8/481; A61B 2034/2063
    See application file for complete search history.

(56) References Cited

U.S. PATENT DOCUMENTS

| | | | |
|---|---|---|---|
| 2006/0041243 A1 | 2/2006 | Nayak | |
| 2006/0100514 A1* | 5/2006 | Lopath | A61B 17/2202 600/458 |

(Continued)

FOREIGN PATENT DOCUMENTS

| | | | | |
|---|---|---|---|---|
| CN | 102917656 A | * | 2/2013 | ..... A61B 17/320068 |

OTHER PUBLICATIONS

Liu, Weizhen, et al. "A novel injectable, cohesive and toughened si-HPMC (silanized-hydroxypropyl methylcellulose) composite calcium phosphate cement for bone substitution". Acta Biomaterialia, vol. 10, No. 7, 2014, p. 3335-3345. https://doi.org/10.1016/j.actbio.2014.03.009.

(Continued)

*Primary Examiner* — Boniface N Nganga
*Assistant Examiner* — Zainab Mohammed Aldarraji
(74) *Attorney, Agent, or Firm* — Matthew J. Smyth

(57) ABSTRACT

A method of performing an ultrasound-guided procedure may include (a) providing a medical device that has (i) a therapeutic distal tip configured to percutaneously alter internal tissue or bone at a treatment site of a patient; (ii) a source of biocompatible fluid; and (iii) a delivery system configured to selectively deliver a quantity of the biocompatible fluid, with echogenic microbubbles therein, to an area external and adjacent to the therapeutic distal tip. The method may further include subcutaneously advancing the therapeutic distal tip toward the treatment site; delivering a quantity of biocompatible fluid with echogenic microbubbles to the area; observing, via ultrasound, an anatomic structure proximate the treatment site and dispersion of the echogenic microbubbles at the area; and based on a nature and location of the dispersion, steering the therapeutic distal tip relative to the anatomic structure, and continuing to advance the therapeutic distal tip toward the treatment site.

20 Claims, 3 Drawing Sheets

(56) References Cited

U.S. PATENT DOCUMENTS

| | | | |
|---|---|---|---|
| 2007/0239027 A1* | 10/2007 | Nita | A61B 17/22012 601/2 |
| 2010/0228122 A1 | 9/2010 | Keenan | |
| 2011/0152836 A1 | 6/2011 | Riopelle | |
| 2011/0160620 A1* | 6/2011 | Gill | A61B 17/320068 601/2 |
| 2011/0201974 A1* | 8/2011 | Soltani | A61B 17/2202 601/2 |
| 2013/0324989 A1* | 12/2013 | Leung | A61B 8/0841 606/24 |
| 2016/0331434 A1* | 11/2016 | Phillips | A61B 34/20 |
| 2018/0036033 A1* | 2/2018 | Ignagni | A61B 17/3468 |
| 2018/0071553 A1* | 3/2018 | Vortman | A61N 7/00 |

OTHER PUBLICATIONS

Macmahon, Peter, et al. "Injectable corticosteroid and local anesthetic preparations: A review for radiologists". Radiology, vol. 252, No. 3, 2009, p. 647-661. https://doi.org/10.1148/radiol.2523081929.

Denis et al., Randomized Double-Blind Controlled Trial Comparing the Effectiveness of Lumbar Transforaminal Epidural Injections of Particulate and Nonparticulate Corticosteroids for Lumbosacral Radicular Pain, 2015, Pain Medicine, 16: 1697-1708.

Bernard et al., "Agitated Saline Contrast Echocardiography in the Identification of Intra- and Extracardiac Shunts: Connecting the Dots," Journal of the American Society of Echocardiography, 2020, 1-11, doi:10.1016/j. echo.2020.09.013.

Cabrelli et al., "Stable phantom materials for ultrasound and optical imaging," Physics in Medicine and Biology, 2017, 432-447, doi: 10.1088/1361-6560/62/2/432.

Cooley et al., "Characterization of the interaction of nanobubble ultrasound contrast agents with human blood components," Bioactive Materials, 2023, 642-652.

Goertz et al., "Attenuation and size distribution measurements of DEFINITY(TM) and manipulated DEFINITY(TM) populations," Ultrasound in Medicine and Biology, 2007, vol. 33, No. 9, 1376-1388, doi: 10.1016/j.ultrasmedbio.2007.03.009.

Kabha and Barak, "Paradoxical Symptomatic Air Embolism after Saline Contrast Transesophageal Echocardiography," Echocardiography: A Journal of CV Ultrasound & Allied Tech., 2008, vol. 25, No. 3, 349-350, doi:10.1111/j.1540-8175.2007.00628.x.

Kubo and Nakata, "Air embolism due to a patent foramen ovale visualized by harmonic contrast enchocardiography," Journal of Neurology, Neurosurgery and Psychiatry, 2001, Neurological Picture, 71:555, doi:10.1136/jnnp.71.4.555.

Kumar et al., "Micro-Bubbles in the Left Heart," Journal of Cardiology & Cardiovascular Therapy, 2017, vol. 8, Issue 5, 1-4, doi:10.19080/JOCCT.2017.08.555748.

Lin et al., "Optimizing Sensitivity of Ultrasound Contrast-Enhanced Super-Resolution Imaging by Tailoring Size Distribution of Microbubble Contrast Agent," Ultrasound in Medicine and Biology, 2017, vol. 43, No. 10, 2488-2493, doi:10.1016/j.ultrasmedbio.2017.05.014.

* cited by examiner

ULTRASOUND-GUIDED PROCEDURES

CROSS-REFERENCE TO RELATED APPLICATIONS

This application claims the benefit of U.S. Provisional Application Ser. No. 63/161,374, titled "Ultrasound-Guided Procedures," filed Mar. 15, 2021. This application incorporates the entire contents of the foregoing application herein by reference.

TECHNICAL FIELD

Various embodiments relate generally to ultrasound-guided procedures.

BACKGROUND

Repetitive motion and use of specific muscles and joints can cause injuries and conditions that affect corresponding muscles, tendons, tendon sheaths, ligaments, bones and other anatomic structures. Muscles and tendons may tear, creating pain and limiting motion; tendons and tendon sheaths may become inflamed, impeding normal functioning of joints. For example, repetitive motion of the fingers, hand and wrist (e.g., through heavy keyboard use) may cause inflammation in various anatomic structures in the wrist, and this inflammation can cause the median nerve to be compressed, causing numbness or pain. As another example, repetitive motion of the shoulder and arm (e.g., throwing or overhead motions associated with recreational or athletic activities) may cause tearing, inflammation, or other injury to various structures in the shoulder, including, for example, the rotator cuff muscles.

Surgical procedures may be employed to treat such injuries. In some cases, open surgery is employed; in other cases, laparoscopic or arthroscopic techniques may be employed; and in still other cases, percutaneous procedures may be employed. Regardless of the technique employed, successful treatment involves treating injured tissue while minimizing trauma to surrounding healthy tissue.

SUMMARY

A method of performing an ultrasound-guided procedure may include (a) providing a medical device that has (i) a therapeutic distal tip configured to percutaneously alter internal tissue or bone at a treatment site of a patient; (ii) a source of biocompatible fluid; and (iii) a delivery system configured to selectively deliver a quantity of the biocompatible fluid, with echogenic microbubbles therein, to an area external and adjacent to the therapeutic distal tip. The method may further include subcutaneously advancing the therapeutic distal tip toward the treatment site; delivering a quantity of biocompatible fluid with echogenic microbubbles to the area; observing, via ultrasound, an anatomic structure proximate the treatment site and dispersion of the echogenic microbubbles at the area; and based on a nature and location of the dispersion, steering the therapeutic distal tip relative to the anatomic structure, and continuing to advance the therapeutic distal tip toward the treatment site.

In some implementations, the therapeutic distal tip is one of a blade, a trochar, a grinding tip, a source of ultrasonic energy, a source of radio frequency energy, or a source of pressurized fluid. The treatment site may include a finger, a wrist, an elbow, a shoulder, a back, a hip, a knee, an ankle, a foot, a toe, or a joint.

The anatomic structure may include a ligament, a tendon, a bone, a band of muscle, a portion of fat, a nerve, a vessel, a duct, a lymph node or a gland. Steering the therapeutic distal tip relative to the anatomic structure may include steering the therapeutic distal tip away from a blood vessel or a nerve.

Observing the dispersion of the echogenic microbubbles may include observing a lateral dispersion of the echogenic microbubbles parallel to a plane of tissue. Observing the dispersion of the echogenic microbubbles may include observing a diffuse dispersion of echogenic microbubbles. Steering the therapeutic distal tip may include steering the therapeutic distal tip along the plane of tissue; alternatively, steering the therapeutic distal tip may include steering the therapeutic distal tip through the plane of tissue.

The method may further include delivering an additional quantity of biocompatible fluid to hydrodissect the plane of tissue from other tissue adjacent the plane. The method may further include evacuating a portion of the quantity or additional quantity through the medical device.

DETAILED DESCRIPTION

Treatment of certain injuries to the muscles, tendons, ligaments and surrounding structures may be provided with one or more percutaneous tools. In some implementations, clinicians use such tools in treating patient conditions under ultrasound guidance. That is, during a treatment procedure, a clinician may employ an ultrasound system (e.g., an ultrasound transducer, manipulated on the surface of a patient over the treatment site, and a corresponding graphical interface) to visualize internal structures at and adjacent to a specific area of treatment—for example, while the clinician is advancing a percutaneous tool to the treatment site and while the clinician is using the percutaneous tool to provide the treatment.

As a specific example, a clinician may perform a ligament release using a percutaneous tool having a retractable blade; and the clinician may monitor the anatomic structures around the target ligament (e.g., nerves, vessels, bands of muscle, ligaments, portions of fat, etc.) using ultrasound. As another example, a clinician may remove necrotic tissue in or around a tendon using a percutaneous tool having an energy source (e.g., ultrasound, radio frequency, laser energy, or pressurized fluid) configured to break down, debride and/or remove the necrotic tissue. As another example, a clinician may remove superfluous calcific deposits from a bone using a percutaneous tool configured to provide direct mechanical debridement (e.g., by grinding or burring).

In each of the foregoing examples, and in the case of percutaneous procedures generally, it may be advantageous to enhance ultrasonic imaging of the tool and the procedure. Given variation in how different internal anatomic structures (e.g., vessels, nerves, muscles, fat, tendons, ligaments, etc.) reflect ultrasound waves, it can be difficult to visualize certain structures. In addition, it can be difficult to differentiate ultrasound images of like adjacent structures, such as discrete bands of overlapping muscles. Accordingly, any features in a device or method that can enhance ultrasound imaging may be advantageous. In this description, various methods and devices for enhancing ultrasound images are described.

Figure 1:
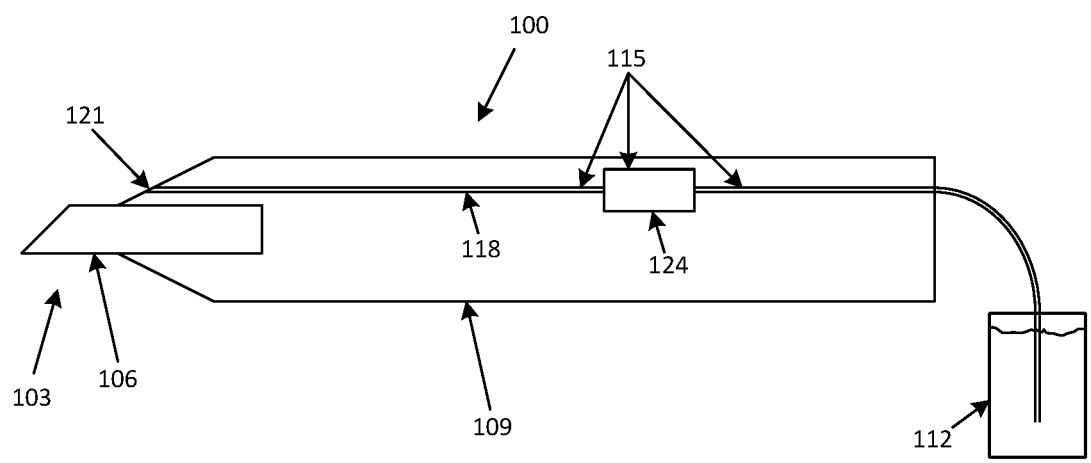
FIG. 1 illustrates an exemplary medical device that can be used to provide therapy to a patient.

FIG. 1 illustrates a medical device 100 that can be used to provide therapy to a patient. As shown, the medical device 100 includes a therapeutic distal tip 103 that may be configured to percutaneously alter internal tissue or bone at a treatment site. In some implementations, the therapeutic distal tip 103 includes a specific tool 106 that facilitates such alteration. For example, the tool 106 could include a retractable blade for cutting tissue, such as ligaments or tendons. As another example, the tool 106 could include a source of energy, such as ultrasound or radio frequency (RF) energy for ablating necrotic tissue. As other examples, the tool 106 could include a blade, a trocar, a grinding or burring tip, or a device for delivering a pressurized flow of fluid.

In some implementations, the tool 106 is partially exterior to a housing 109 of the medical device 100 and partially interior to the housing 109. In other implementations, the tool may be fully enclosed within the housing 109 (e.g., as in the case of an ultrasonic or RF energy source, where the energy may be transmitted, conducted or communicated to an area outside of and adjacent the therapeutic distal tip 103). As shown, the tool 100 may not be to scale or proportion; and in some implementations, a portion of the housing 109 and the therapeutic distal tip 103 may both be configured for subcutaneous access to internal tissue and structures of a patient.

As shown, the medical device 100 also includes a source 112 of biocompatible fluid. In some implementations, the biocompatible fluid may be saline. In other implementations, the biocompatible fluid may be purified water or a dextrose solution. In other implementations, the biocompatible fluid may include platelet rich plasma (PRP) or stem cells that may promote healing of a target treatment area. In other implementations, the biocompatible fluid may include an anesthetic, such as lidocaine.

The medical device 100 may further include a delivery system 115 configured to selectively deliver (e.g., upon clinician activation of the delivery system) a quantity of the biocompatible fluid to an area external and adjacent the therapeutic distal tip 103. In some implementations, the delivery system 115 includes a lumen 118 that couples the source 112 to a port 121 at the therapeutic distal tip 103. The delivery system 115 may further include a pump or device for pressurizing fluid at the source 112, such that a quantity of biocompatible fluid can be selectively delivered to the port 121. As shown, the delivery system 115 is disposed within the housing 109 of the medical device; but in other implementations, the delivery system 115 is disposed external to, or partially external to, the housing 109.

The medical device 100 may further include a device 124 for creating echogenic microbubbles in the biocompatible fluid—either at the source 112 (not shown), within the delivery system 115 (as shown), or at another point between the source 112 and the device 124 (not shown).

In some implementations, such echogenic microbubbles appear clearly under ultrasonic imaging and can facilitate visualization of adjacent anatomic structures. Dispersion of the microbubbles can be monitored under ultrasound, and the nature and location of the dispersion can provide valuable information to the clinician regarding the current position of the therapeutic distal tip 103.

In some implementations, the device 124 for creating echogenic microbubbles is an aerator that creates such microbubbles in the biocompatible fluid as the biocompatible fluid passes through the device 124 or the delivery system 115. For example, the device 124 may include a venturi (not shown) that draws air or other gas into a stream of biocompatible fluid as that stream passes through the venturi throat. As another example, the device 124 may include a pressurized source of air or gas that is injected into the biocompatible fluid to create microbubbles. As another example, the device 124 may include an ultrasonic or piezoelectric agitator that, when actuated, introduces microbubbles into the biocompatible fluid.

Figure 2:
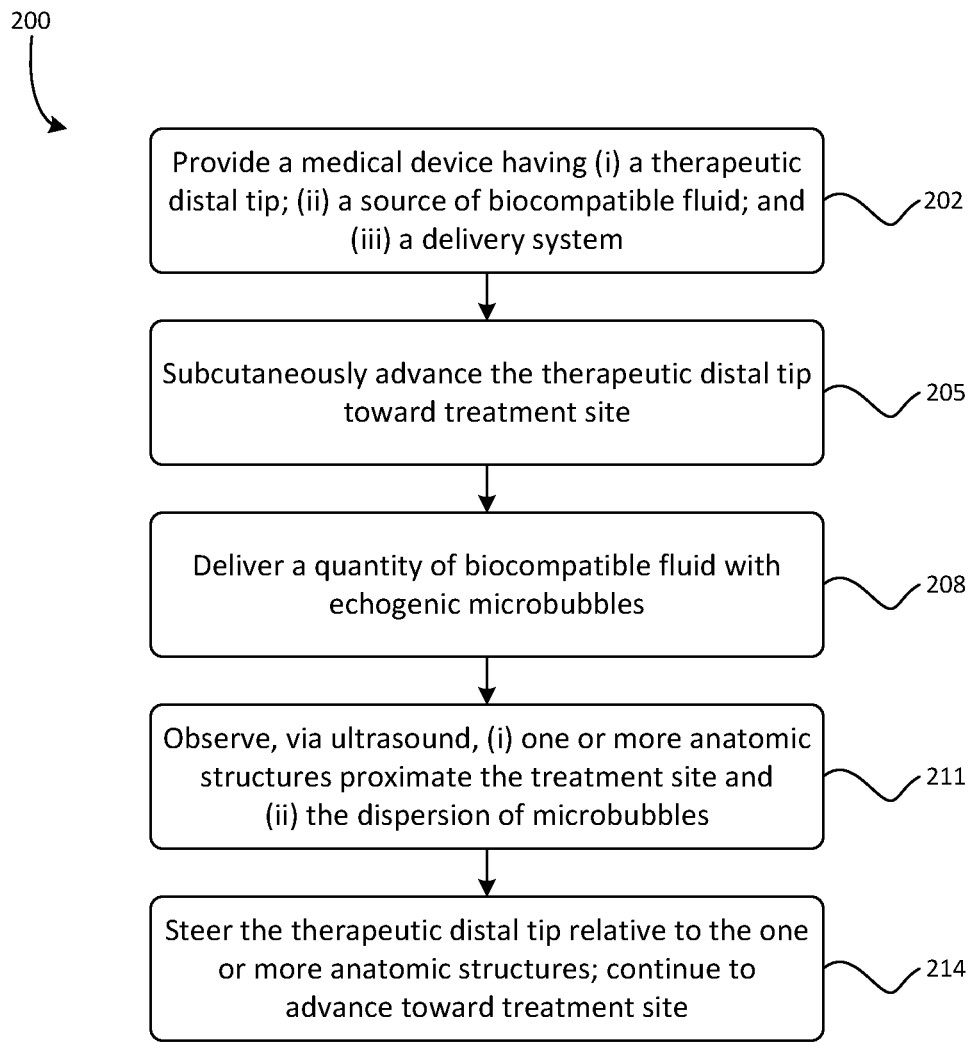
FIG. 2 depicts an exemplary method for using a medical device to provide therapy to a patient.

FIG. 2 depicts an exemplary method 200 for using a device, such as the medical device 100 illustrated in and described with reference to FIG. 1. As shown, the method 200 includes providing (202) a medical device having (i) a therapeutic distal tip configured to percutaneously alter internal tissue or bone at a treatment site of a patient; (ii) a source of biocompatible fluid; and (iii) a delivery system configured to selectively deliver a quantity of biocompatible fluid with echogenic microbubbles therein, to an area external and adjacent the therapeutic distal top. In some implementations, a device such as the medical device 100 is provided (202).

The method 200 may include subcutaneously advancing (205) the therapeutic distal tip toward the treatment site. In one exemplary procedure, the therapeutic distal tip may be advanced through the carpal tunnel of a patient's wrist, toward and under the transverse carpal ligament (e.g., to facilitate subsequent release of the transverse carpal ligament). In another exemplary procedure, the therapeutic distal tip may be advanced toward the A1 pulley of a patient's finger (e.g., to facilitate subsequent release of the same, for treatment of trigger finger). In another exemplary procedure, the therapeutic distal tip may be advanced toward necrotic tissue of a tendon (e.g., to facilitate a subsequent tenotomy). In another exemplary procedure, the therapeutic distal tip may be advanced toward inflamed tissue of a patient's plantar fascia (e.g., to facilitate subsequent breakdown and removal of scar tissue and promotion of additional blood perfusion to the treatment area). Various other procedures may be facilitated using the method 200 depicted, including procedures that provide therapy to patients' fingers, wrists, arms, elbows, shoulders, necks, backs, hips, knees, ankles, feet, toes, etc.

The method 200 may include delivering (208) a quantity of biocompatible fluid with echogenic microbubbles to an area external to and adjacent the therapeutic distal tip. For example, with reference to FIG. 1, biocompatible fluid from the source 112 may be delivered, via the delivery system 115, out the port 121.

In some implementations, the quantity of biocompatible fluid is delivered (208) as the therapeutic distal tip is advanced toward the treatment site. For example, a clinician may cause (e.g., by actuating a delivery system) a small quantity of biocompatible fluid with echogenic microbubbles to be released at the therapeutic distal tip, to enhance imaging around the same. In some implementations, the clinician may periodically pause the advancing (205) of the therapeutic distal tip to deliver (208) a quantity of the biocompatible fluid with echogenic microbubbles.

The method 200 may include observing (211), via ultrasound, one or more anatomic structures proximate the treatment site and dispersion of the microbubbles. In some implementations, observing (211) the nature and dispersion of the microbubbles can be particularly helpful to the clinician in orienting the therapeutic distal tip and in avoiding trauma to anatomic structures adjacent the area of treatment.

Figure 3A:
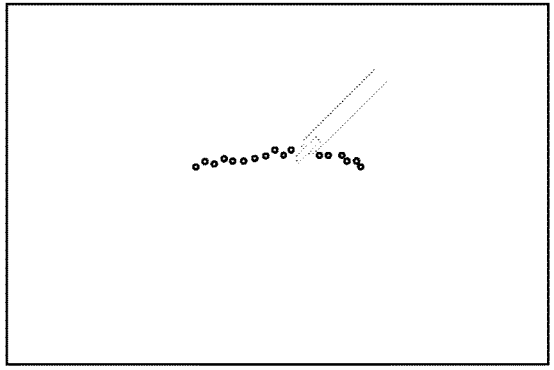
FIG. 3A depicts an exemplary lateral dispersion of microbubbles, as seen under ultrasound guidance.

For example, lateral dispersal of microbubbles can indicate a position of the therapeutic distal tip that is adjacent a plane of tissue (e.g., a specific ligament or band of muscle). An exemplary (exaggerated) lateral dispersal of microbubbles, as the microbubbles themselves may appear under ultrasound (with background imaging removed) is depicted in FIG. 3A. The visual confirmation provided by such a lateral dispersal of microbubbles, as seen on ultrasound, can, for example, guide a clinician in either steering the therapeutic distal tip along the plane of tissue, or guide the clinician in continuing to advance the therapeutic distal tip through the plane of tissue or deeper relative to the plane of tissue.

In some implementations, an additional quantity of biocompatible fluid may be delivered (208) to hydrodissect one plane of tissue relative to another plane of tissue, or one structure relative to another adjacent structure or tissue.

Figure 3B:
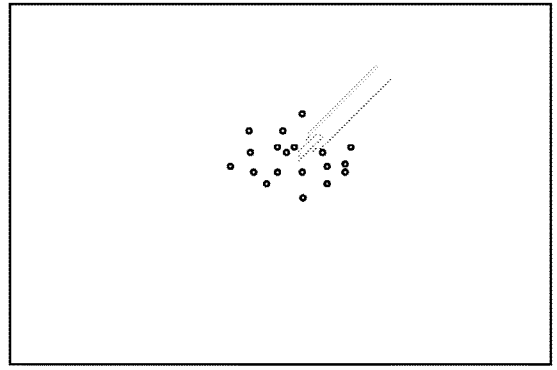
FIG. 3B depicts an exemplary diffuse dispersion of microbubbles.
Figure 3C:
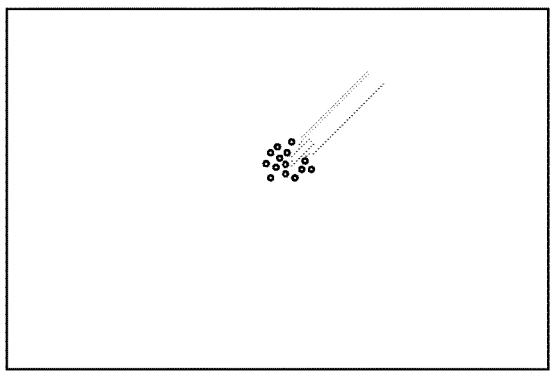
FIG. 3C depicts another exemplary diffuse dispersion of microbubbles.

Diffuse dispersal of microbubbles, as seen on ultrasound, may provide other guidance. For example, a diffuse dispersal of microbubbles may provide confirmation to a clinician that the therapeutic distal tip is in an interstitial space or within tissue. More particularly, a relatively broad, diffuse dispersion (as depicted in FIG. 3B) may indicate a position within an interstitial space; whereas a relatively tight, diffuse dispersion (as depicted in FIG. 3C) may indicate a position within tissue (e.g., a muscle, tendon or ligament).

Figure 3D:
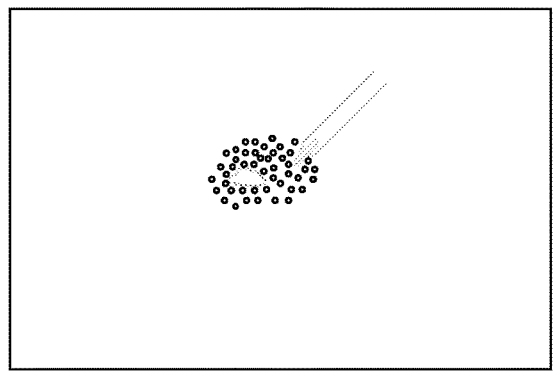
FIG. 3D depicts microbubbles outlining an exterior of an anatomic structure, in an exemplary implementation.
Figure 3E:
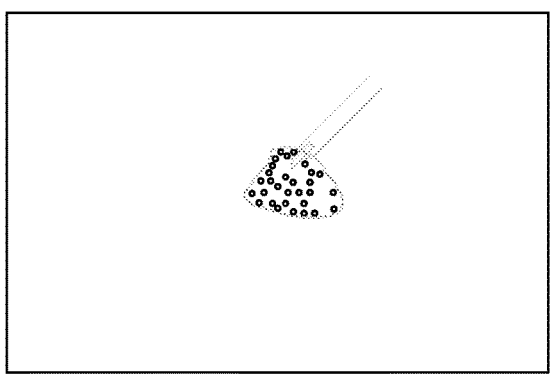
FIG. 3E depicts microbubbles outlining an interior of an anatomic structure, in an exemplary implementation.

In areas where microbubbles disperse in a diffuse manner, such dispersion may outline other structures (e.g., vessels, nerves, tissue boundaries, bursa envelopes, etc.; see FIG. 3D as an example depiction of microbubbles outlining a structure from the exterior; see FIG. 3E as an example depiction of microbubbles outlining an envelope, such as a bursa or capsule, from the interior of the structure).

The visual information provided by the echogenic microbubbles may assist the clinician in more precisely pinpointing an anatomic location near the treatment site. This enhanced precision, relative to a procedure without echogenic microbubbles, may minimize trauma to surrounding anatomic structures and may further confirm delivery of therapy in the precise location intended.

In some implementations, a portion of the quantity of biocompatible fluid delivered may be evacuated from a region adjacent the therapeutic distal tip. For example, the biocompatible fluid may be evacuated via additional lumen (s) (not shown in FIG. 1) that may be present in the medical device. As a more specific example, some medical devices that are configured for removing necrotic tissue may include other lumens for irrigating a treatment site and for evacuating detritus from the site. In some implementations, lumen (s) already existing for such purposes may also be employed to deliver biocompatible fluid with echogenic microbubbles, as described.

The method 200 may include—based on a nature and location of the dispersion—steering (214), the therapeutic distal tip relative to the anatomic structure, and continuing to advance (214) the therapeutic distal tip toward the treatment site. As mentioned above, in some implementations, the therapeutic distal tip may be steered (214) along a plane of tissue; in other implementations, the therapeutic distal tip may be steered (214) through a plane of tissue; in other implementations, the therapeutic distal tip may be steered (214) around or away from vessels, nerves, ducts, glands, lymph nodes, or other structures.

Several implementations have been described with reference to exemplary aspects, but it will be understood by those skilled in the art that various changes may be made and equivalents may be substituted for elements thereof without departing from the contemplated scope. For example, in some implementations, the medical devices described herein may comprise various surgical tools configured for performing procedures related to orthopedics and sports medicine; in other implementations, the medical device may comprise a syringe equipped with a device to aerate fluid contained therein with microbubbles as that fluid is delivered subcutaneously to an internal structure of a patient.

In some implementations, the biocompatible fluid may primarily serve as an irrigation agent or to provide enhanced ultrasound contrast. In other implementations, the biocompatible fluid may itself deliver therapeutic benefit—for example, the biocompatible fluid may comprise a therapeutic agent, such as a pharmaceutical preparation, platelet rich plasma (PRP), stem cells, a corticosteroid, etc.; and echogenic microbubbles may be added thereto. The echogenic microbubbles may assist a clinician in delivering the therapeutic biocompatible fluid to its intended target site; and the echogenic microbubbles may be further employed to confirm delivery to the intended site (e.g., by confirming delivery to tissue or to a bursa/capsule, as depicted in FIG. 3C or FIG. 3E, respectively).

Many other variations are possible, and modifications may be made to adapt a particular situation or material to the teachings provided herein without departing from the essential scope thereof. Therefore, it is intended that the scope include all aspects falling within the scope of the appended claims.

What is claimed is:

1. A method of performing an ultrasound-guided procedure, the method comprising:
   providing a medical device, the medical device comprising (i) a therapeutic distal tip configured to percutaneously alter internal tissue or bone at a treatment site of a patient; (ii) a source of biocompatible fluid; and (iii) a delivery system configured to selectively deliver a quantity of the biocompatible fluid, with echogenic microbubbles therein, to an area external and adjacent to the therapeutic distal tip;
   subcutaneously advancing the therapeutic distal tip toward the treatment site;
   delivering a quantity of biocompatible fluid with echogenic microbubbles to the area;
   observing, via ultrasound, an anatomic structure proximate the treatment site and dispersion of the echogenic microbubbles at the area; and
   based on a nature and location of the dispersion, steering the therapeutic distal tip relative to the anatomic structure, and continuing to advance the therapeutic distal tip toward the treatment site.

2. The method of claim 1, wherein the therapeutic distal tip comprises one of a blade, a trochar, a grinding tip, a source of ultrasonic energy, a source of radio frequency energy, and a source of pressurized fluid.

3. The method of claim 1, wherein the treatment site comprises a finger, a wrist, an elbow, a shoulder, a back, a hip, a knee, an ankle, a foot, a toe, or a joint.

4. The method of claim 1, wherein the anatomic structure comprises a ligament, a tendon, a bone, a band of muscle, a portion of fat, a nerve, a vessel, a duct, a lymph node or a gland.

5. The method of claim 1, wherein steering the therapeutic distal tip relative to the anatomic structure comprises steering the therapeutic distal tip away from a blood vessel or a nerve.

6. The method of claim 1, wherein observing the dispersion of the echogenic microbubbles comprises observing a lateral dispersion of the echogenic microbubbles parallel to a plane of tissue.

7. The method of claim 6, wherein steering the therapeutic distal tip comprises steering the therapeutic distal tip along the plane of tissue.

8. The method of claim 6, wherein steering the therapeutic distal tip comprises steering the therapeutic distal tip through the plane of tissue.

9. The method of claim 6, further comprising delivering an additional quantity of biocompatible fluid to hydrodissect the plane of tissue from other tissue adjacent the plane.

10. The method of claim 1, wherein observing the dispersion of the echogenic microbubbles comprises observing a diffuse dispersion of echogenic microbubbles.

11. The method of claim 9, further comprising evacuating a portion of the quantity or additional quantity of biocompatible fluid through the medical device.

12. A method of performing an ultrasound-guided procedure, the method comprising:
    providing a medical device, the medical device comprising (i) a therapeutic distal tip configured to treat tissue or bone within a bursa or a capsule at a treatment site of a patient; (ii) a source of biocompatible fluid; and (iii) a delivery system configured to selectively deliver a quantity of the biocompatible fluid, with echogenic microbubbles therein, to an area external and adjacent to the therapeutic distal tip;
    subcutaneously advancing the therapeutic distal tip toward the treatment site;
    delivering a quantity of biocompatible fluid with echogenic microbubbles to the area;
    observing, via ultrasound, dispersion of the echogenic microbubbles at the area;
    based on a nature and location of the dispersion, steering the therapeutic distal tip toward the treatment site;
    delivering an additional quantity of biocompatible fluid with echogenic microbubbles to the area; and
    observing, via ultrasound, a diffuse dispersion of the echogenic microbubbles at the area outlining an envelope, from an interior of the envelope, thereby confirming the delivering of the additional quantity of biocompatible fluid to within the bursa or the capsule.

13. The method of claim 12, wherein the biocompatible fluid comprises at least one of a pharmaceutical preparation, a platelet rich plasma, stems cells or a corticosteroid.

14. The method of claim 12, wherein steering the therapeutic distal tip toward the treatment site comprises steering the therapeutic distal tip along a plane of tissue.

15. The method of claim 12, wherein steering the therapeutic distal tip toward the treatment site comprises steering the therapeutic distal tip through a plane of tissue.

16. The method of claim 12, wherein steering the therapeutic distal tip toward the treatment site comprises steering the therapeutic distal tip away from a blood vessel or a nerve.

17. A method of performing an ultrasound-guided procedure, the method comprising:
    providing a medical device, the medical device comprising (i) a therapeutic distal tip configured to treat tissue or bone at a treatment site of a patient; (ii) a source of biocompatible fluid; and (iii) a delivery system configured to selectively deliver a quantity of the biocompatible fluid, with echogenic microbubbles therein, to an area external and adjacent to the therapeutic distal tip;
    subcutaneously advancing the therapeutic distal tip toward the treatment site;
    delivering a quantity of biocompatible fluid with echogenic microbubbles to the area;
    observing, via ultrasound, a lateral dispersion of the echogenic microbubbles at the area, adjacent a plane of tissue;
    based on a nature and location of the dispersion, advancing the therapeutic distal tip through the plane of tissue, toward the treatment site; and
    delivering at least one of a pharmaceutical preparation, a platelet rich plasma, stem cells or a corticosteroid.

18. The method of claim 17, further comprising delivering an additional quantity of biocompatible fluid to hydrodissect the plane of tissue from other tissue adjacent the plane.

19. The method of claim 17, further comprising delivering an additional quantity of biocompatible fluid, with echogenic microbubbles therein; and observing, via ultrasound, a tight, diffuse dispersion of the echogenic microbubbles at the area, thereby confirming the delivering of the at least one of the pharmaceutical preparation, the platelet rich plasma, the stem cells or the corticosteroid to tissue at the treatment site.

20. The method of claim 17, further comprising delivering an additional quantity of biocompatible fluid, with echogenic microbubbles therein; and observing, via ultrasound, a diffuse dispersion of the echogenic microbubbles at the area outlining an envelope, from an interior of the envelope, thereby confirming the delivering of the at least one of the pharmaceutical preparation, the platelet rich plasma, the stem cells or the corticosteroid in a bursa or capsule beyond the plane of tissue.

\* \* \* \* \*